United States Patent [19]

Stönner et al.

[11] 4,218,576
[45] * Aug. 19, 1980

[54] PROCESS OF SCRUBBING POLYVALENT PHENOLS FROM GAS

[75] Inventors: Hans-Martin Stönner, Schwalbach; Paul Wiesner, Oberursel, both of Fed. Rep. of Germany

[73] Assignee: Metallgesellschaft Aktiengesellschaft, Frankfurt am Main, Fed. Rep. of Germany

[*] Notice: The portion of the term of this patent subsequent to Jun. 27, 1995, has been disclaimed.

[21] Appl. No.: 682,035

[22] Filed: Apr. 30, 1976

Related U.S. Application Data

[63] Continuation-in-part of Ser. No. 486,998, Jul. 10, 1974, Pat. No. 4,097,539.

[30] Foreign Application Priority Data

Dec. 28, 1973 [DE] Fed. Rep. of Germany ....... 2365064

[51] Int. Cl.$^2$ .............................................. C07C 37/34
[52] U.S. Cl. .................................................. 568/751
[58] Field of Search .......... 260/621 A, 627 G, 621 B, 260/627 H, 627 R, 624 A; 568/751

[56] References Cited

PUBLICATIONS

Wett, The Oil and Gas Journal, Jun. 25, 1973, pp. 131-134.

Primary Examiner—Werren B. Lone
Attorney, Agent, or Firm—Karl F. Ross

[57] ABSTRACT

Mono and polyvalent phenols are recovered from gasified coal by scrubbing the phenol-containing gas with water, separating the extracted phenols into a monovalent phenol-rich fraction and a polyvalent phenol-rich fraction and recovering the monovalent phenols separately from the polyvalent phenols by solvent extraction.

7 Claims, 1 Drawing Figure

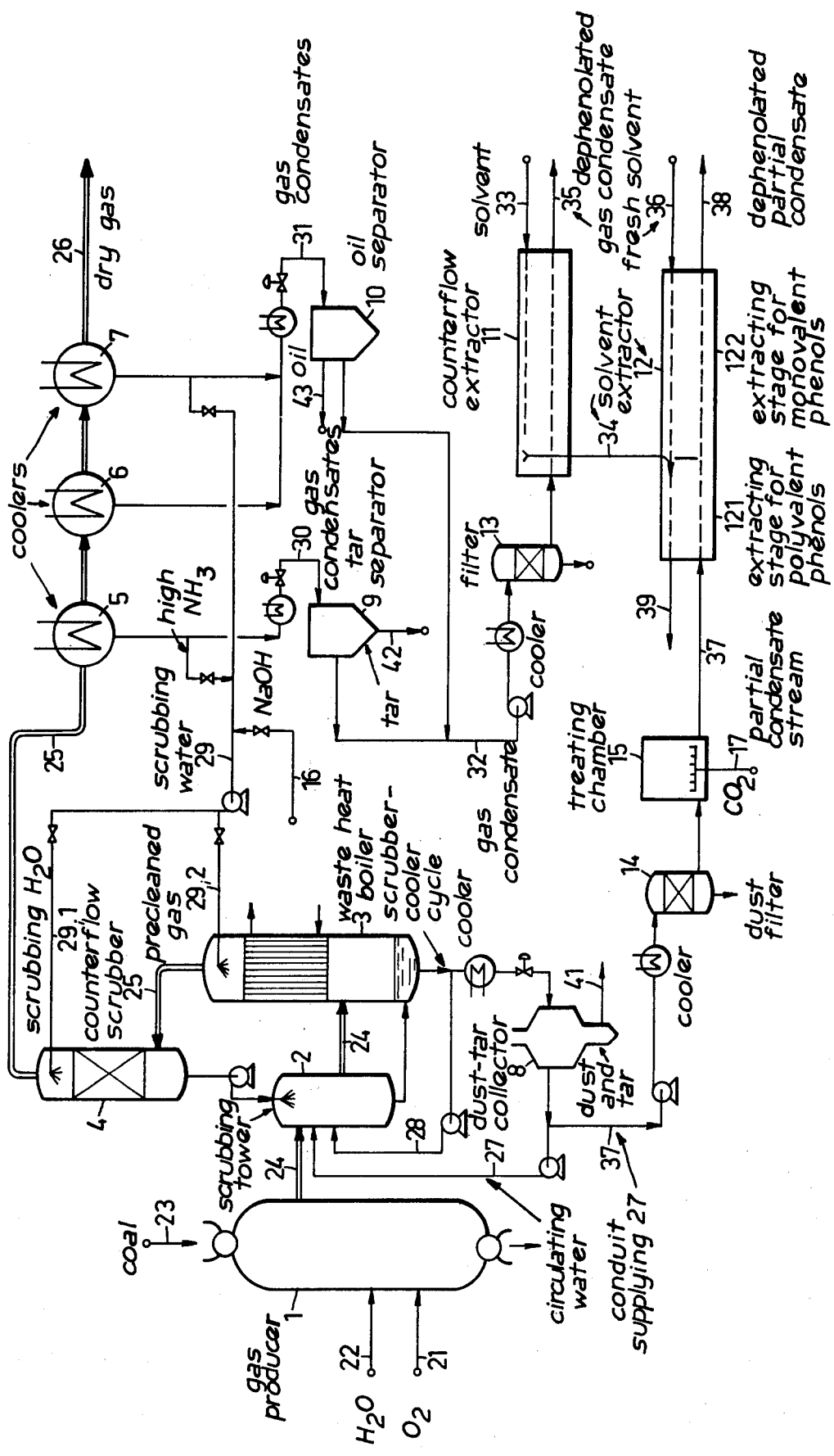

PROCESS OF SCRUBBING POLYVALENT PHENOLS FROM GAS

CROSS-REFERENCE TO RELATED APPLICATION

This application is a continuation-in-part of Ser. No. 486,998 filed July 10, 1974 now U.S. Pat. No. 4,097,539.

FIELD OF THE INVENTION

The invention relates to a process of scrubbing polyvalent phenols from gas produced by pressure gasification and of extracting these phenols from the scrubbing water, in a process in which the gas is produced in known manner under pressure from coal, oxygen and water vapor and is scrubbed and subjected to fractional condensation to form condensates which contain mon- and polyvalent phenols, $NH_3$, $CO_2$, $H_2S$, HCN, fixed salts of $NH_3$ mainly with Cl, F, and fatty acids, as well as dust, tar and oil, and in which the condensates are separately collected, sub-cooled, flashed and subjected to a treatment to collect dust, tar, and oil, then cooled further, filtered and subsequently subjected to an extraction of phenol.

BACKGROUND OF THE INVENTION

The gas condensate produced in conjunction with the pressure gasification of coal contains various substances which pollute the environment, such as free $NH_3$ or combined $NH_3$, $H_2S$, HCN, and mono- and polyvalent phenols in addition to fatty acids, chlorides, fluorides, tars, oil and dust. That gas liquor cannot readily be discarded because it contains valuable substances, which can be recovered, as well as many noxious substances, which must be removed from the gas liquor except for low residual contents in order to avoid an unnecessary pollution of the underground water and river water or to enable a further use thereof.

The tars and oils are removed by separation and filtration and are separately sold or burned.

Dust is returned to the pressure gasification process and enters the ash.

Free ammonia ($NH_3$) is driven off and concentrated or burned.

$CO_2$ and $H_2S$ as well as HCN are also driven off and supplied, e.g., to a plant for producing sulfur.

The monovalent phenols are preferably extracted to a few ppm and are recovered. (See LURGI Handbook 1970, Chapter 2.1, published by LURGI, Frankfurt-on-Main; Erdol und Kohle, 13, 1960, pages 252–257.)

Upon the removal of the monovalent phenols, part of the polyvalent phenols are removed too. The remainder remains in the water together with the fixed $NH_3$, which is mainly combined with fatty acid or is present as chloride and fluoride. The poor extraction of the polyvalent phenols is due to the fact that the partition coefficients are, on an average, lower by about one power of ten than the partition coefficients for monovalent phenols.

A disproportionately large solvent circulation would be required for a recovery also of the polyvalent phenols.

The extraction plant is normally followed by a biological afterpurification plant. These processes for removing the remaining polyvalent phenols are uneconomical and as far as the biological processes are concerned require great experience as regards the provision and preservation of the biologically active sludge.

If the phenols are recovered in an alkaline process, the resulting phenolate must be dissociated.

OBJECT OF THE INVENTION

It is the object of the present invention to overcome these disadvantages and to provide an improved process particularly for the extraction of polyvalent phenols.

SUMMARY OF THE INVENTION

This object is accomplished in that the condensate formed at a high temperature before the flashing step and containing a major portion of the polyvalent phenols is subjected to a separate solvent extraction of phenols.

According to a preferred feature of the invention the solvent which has been used for extraction of phenols from the condensates formed at low temperature, which solvent is preladen with monovalent phenols, is used as a solvent for extracting the polyvalent phenols in part of the extraction stages.

It has been found that a predominant part of the polyvalent phenols can be extracted without an increase of the quantity of solvent required for removing the monovalent phenols and with the same solvent if a partial stream produced by the fractionating condensation of the gas liquor from the gas produced by pressure gasification, which partial stream contains a major part of the polyvalent phenols, is separately collected and treated. That partial stream is then treated first with the solvent used for the extraction of the remaining quantity of gas condensate, which solvent is already laden with monovalent phenols, and said partial stream is subsequently after-treated in known manner with a comparatively small quantity of clean solvent to remove the monovalent phenols. The remaining quantity of gas condensate may be about 7–15 times the amount of said partial stream.

In this case, the solvent ratio obtained in the first part of the extracting plant is sufficiently high for the extraction of the polyvalent phenols. That solvent ratio is calculated according to the following formula:

$$\frac{L}{TK} = \frac{v(GK - TK) + vTK}{TL} = v\frac{GK}{TK}$$

wherein
GK=total quantity of gas condensate,
TK=quantity of gas condensate which contains a major part of the polyvalent phenols,
v=solvent ratio for the extraction of monovalent phenols, and
L=solvent ratio in the part for extracting polyvalent phenols.

The quantity of solvent $L = v \times GK$ equals that quantity of solvent which is normally required to extract the monovalent phenols from the entire gas condensate. As a result, the plants for recovering the solvent and its steam requirement remain unchanged and the plant size need not be increased.

Besides, the ratio of fresh solvent used for the extraction of the phenols from the partial condensate stream may be greatly increased whereas the total quantity of solvent increases relatively slightly. For this reason the process according to the invention permits a selective extraction and an improved utilization of the solvent.

According to another preferred feature of the invention the polyvalent phenols and the remaining disturbing impurities are removed in additional counterflow stages for scrubbing the gas with water.

According to a further feature of the invention the counterflow scrubbing is effected in a waste heat boiler.

It has been found that the quantity of the polyvalent phenols in the partial stream TK may be increased further if the gas cooler contains a counterflow scrubber having a plurality of theoretical plates, and preferably the same quantity of scrubbing water is used which is required to remove the partial quantity of condensate TK. The scrubbing water may consist of condensate from the primary cooling stage following the wet dust collector and the waste heat boiler. If an additional counterflow scrubber is not installed, the waste heat boiler is suitably designed as a counterflow scrubber.

According to another preferred feature of the invention the scrubbing is accomplished in the counterflow scrubber or waste heat boiler by means of gas condensate from the gas cooler.

The process according to the invention may be improved if scrubbing water is used for scrubbing in the counterflow cooler or waste heat boiler in a quantity which corresponds to a separately removed condensate amounting to 5–30% of the entire condensate produced by the cooling of the gas.

The scrubbing effect may be improved if gas condensate having a high $NH_3$ content and obtained from the cooler part of the gas cooler is used in accordance with the invention as scrubbing water. This has the further advantage that a secondary effect is produced which resides in the removal of the fatty acid salts and halides to a higher degree. Because the remaining gas water (GK−TK) is free of fixed salts, it is much more attractive for further use, particularly as cooling water. This is of special interest in plants erected in dry regions.

According to a further modification of the process according to the invention, NaOH is added to the scrubbing water. This results also in a removal of fatty acid salts and halides to a higher degree. On the other hand, some phenols are then transformed to sodium phenolate, which must be dissociated in an intermediate stage, e.g., by a treatment with separately recovered $CO_2$. That treatment will be particularly recommendable if in addition to the polyvalent phenols a maximum of fixed $NH_3$ salts is to be kept from the remaining gas condensate.

It is desirable to carry out the process according to the invention in that the polyvalent phenols are extracted with preladen solvent in four to ten stages and the monovalent phenols are subsequently extracted in four to ten hours.

All solvents capable of selectively extracting phenols from the wash water of the scrubbing of coal-gasification gases, or the liquids obtained by condensation thereof, have improved capacity to extract phenols when used in accordance with this invention.

BRIEF DESCRIPTION OF THE DRAWING

Hereinafter, a plant will be described which may be used for carrying out an illustrative embodiment of the process according to the invention, reference being made to the sole FIGURE of the drawing which is a flow diagram.

SPECIFIC DESCRIPTION

Gas is produced by a pressure gasification of coal 23 with oxygen 21 and water vapor 22 in a gas producer 1 and contains, inter alia, water vapor and all substances mentioned hereinbefore, from $NH_3$ to dust (see Lurgi Handbuch). The gas 24 produced by pressure gasification is precleaned and cooled in a first scrubbing and cooling stage, which comprises a scrubbing tower 2, a waste heat boiler 3 and a counterflow scrubber 4, to form a precleaned gas 25 produced by pressure gasification, from which additional condensible constituents are removed in an indirect second cooling stage, which comprises coolers 5, 6 and 7, before the gas leaves the gas producer as a dry gas 26. The dust and condensed tar removed in the scrubbing cooler 2, the waste heat boiler 3, (see 11-5 of Perry's Chemical Engineers' Handbook, McGraw-Hill Book Co., New York, 1963) and the counterflow scrubber 4 from the gas 24 produced by pressure gasification are transferred into the draining gas condensate, in which some of the abovementioned constituents are dissolved. The withdrawn gas condensate flows through means for collecting dust, tar and oil and is then recycled as circulating water 27 to the scrubber-cooler. A certain part of said scrubbing water is supplied in conduit 37 to another tar and dust filter 14 connected to the stage 121 for extracting polyvalent phenols.

In the counterflow scrubber 4 the gas is scrubbed with the gas condensate from the indirect cooling stages 5, 6 and 7. Primary condensate from the cooler 5 or high-$NH_3$ condensate from the cooler 7 and/or scrubbing water: 29 or 29.1 additionally enriched with NaOH 16 may be used in the counterflow scrubber and 29.2 in the waste heat boiler. The rate at which condensate is supplied to the counterflow scrubber 4 and the waste heat boiler 3 is selected so that a partial condensate stream 37 is circulated which is about 1/7 to 1/15 of the total gas condensate. The scrubber-cooler cycle 28 and the scrubbing water 27 supplied to the scrubber-cooler are adjusted so that the dust can be reliably discharged and can be separated in the dust-tar collector 8. The dust—tar 41 is supplied to the gas producer 1.

The oil- and tar-containing gas condensates 30, 31 flowing from the gas coolers 5, 6 and 7 are passed through the tar separator 9 and oil separator 10 in such a manner that mainly tar 42 is collected in the tar separator and mainly oil 43 is collected in the oil separator. These separated products are collected in tanks and supplied for further use.

The gas condensate 32 from which oil and tar have been removed in a high degree is supplied through filter 13 to a counterflow extractor 11 and leaves the extractor as a dephenolized gas condensate 35, which is passed through a plant, not shown, for a recovery of solvent and for stripping $H_2S$, $CO_2$, HCN, and $NH_3$ and is then supplied for further use, e.g., as cooling water, or may be discharged as sewage, possibly after a biological aftercleaning.

The solvent 33 consists, e.g., of diisopropyl ether, which flows in a countercurrent to the gas condensate 32–35 through the about ten extracting stages and leaves the extractor as a solvent 34 which is laden with mainly monovalent phenols and is used further as a solvent for polyvalent phenols.

The partial condensate stream 37 is passed through the filter 14 for a removal of remaining tar and dust and is then supplied to the extractor 12 for an initial extraction 121 of polyvalent phenols and a subsequent extraction 122 of monovalent phenols. If NaOH is supplied at 16, the phenolate must be dissociated in the treating chamber 15 by an addition of $CO_2$ 17 so that it can be extracted as phenol. In the part 121, the combined solvents 34 and 36 serve to extract mainly the polyvalent phenols. The partial condensate stream flowing from part 121 into part 122 still contains monovalent phenols in a quantity which is in equilibrium with the phenols contained in the laden solvent 34 plus 36.

In the following extraction stages 122, these "equilibrium phenols" are extracted with the fresh solvent 36. The dephenolized partial condensate stream 38 has a small content of residual phenol and contains the fixed $NH_3$ salts which have been removed in high concentration in the scrubbing tower 4.

This partial stream which is relatively small compared to the total gas condensate may now be subjected to an economical special treatment for producing an ecologically satisfactory sewage. The contents of free $NH_3$ and other gases are very low because the partial pressures thereof at the temperatures in the scrubbers 2, 3 and 4 are so high that these substances remain mainly in the gas and are dissolved in the gas condensate only in the cooler portion of the gas cooler.

The following tables represent two numerical examples. EXAMPLE I relates to the extraction of phenols without the stages 121 for polyvalent phenols and EXAMPLE II with the extractor part 121 for polyvalent phenols.

The extractor 11 consisted of 10 extracting stages and the extractor 12 of 10 stages 122 and 5 stages 121.

EXAMPLE I

Without utilization of extract 34

| Stream (Sole Drawing Figure) | Water Metric tons per hour | Solvent kg/h | Monovalent phenols kg/h | Polyvalent phenols kg/h |
| --- | --- | --- | --- | --- |
| 32 | 1,000. | 0 | 5,350 | 600 |
| 33 | 0.75 | 80,000 | 0 | 0 |
| 34 | 2.45 | 73,000 | 5,330 | 180 |
| 35 | 998.30 | 7,000 | 20 | 420 |
| 36 | 0.075 | 8,000 | 0 | 0 |
| 37 | 100. | 0 | 60 | 200 |
| 38 | 99.825 | 700 | 2 | 160 |
| 39 (without) | 0.25 | 7,300 | 58 | 40 |

EXAMPLE II

With utilization of extract 34

| Stream (Sole Drawing Figure) | Water Metric tons per hour | Solvent kg/h | Monovalent phenols kg/h | Polyvalent phenols kg/h |
| --- | --- | --- | --- | --- |
| 32 | 1,000. | 0 | 5,350 | 600 |
| 33 | 0.75 | 80,000 | 0 | 0 |
| 34 | 2.45 | 73,000 | 5,330 | 180 |
| 35 | 998.30 | 7,000 | 20 | 420 |
| 36 | 0.075 | 8,000 | 0 | 0 |
| 37 | 100. | 0 | 60 | 200 |
| 38 | 99.275 | 700 | 1 | 32 |
| 39 (with) | 3.25 | 80,300 | 5,389 | 348 |

As is apparent from lines 35 and 38 of Tables I and II, the content of monovalent phenols in the extracted water is reduced from 20 ppm to 10 ppm and the content of polyvalent phenols in the extracted water from 1,600 ppm to 320 ppm.

In 11 and in part 122 of 12 the solvent ratio is 8% (33, 36). In part 121 (Example II) it increases to 80.9 without an increase of the circulation of the total solvent.

The same process as disclosed hereinabove was carried out except that the solvent (33) instead of being diisopropyl ether was selected from the following group:
n-butylacetate;
isobutylacetate;
methyl-isobutyl ketone;
benzene; and
n-hexanol The same superior results in the extraction of polyphenols with the monophenol-laden solvent were obtained as shown in Example II. Also, while n-hexanol was one specific alcohol employed as solvent, any water-insoluble, straight or branched chain $C_5$ to $C_{11}$ alcohol will function equivalently.

We claim:

1. A process for the recovery of phenols in admixture with an extraction solvent which comprises the steps of:
   (a) deriving from the pressure gasification of coal and gas containing in addition to monovalent a polyvalent phenols, ammonia, carbon dioxide, hydrogen sulfide, ammonia salts with chlorine and fluorine, fatty acids, dust, tars and oils as impurities;
   (b) scrubbing the gas derived in step (a) with water to produce a scrubbing aqueous mixture containing some of said impurities and some of said phenols, thereby producing a precleaned gas;
   (c) cooling the precleaned gas to remove impurities therefrom;
   (d) condensing a phenolic fraction from the cooled precleaned gas and removing tar and oil from the resulting condensate, said condensate constituting an aqueous mixture relatively rich in monovalent phenols;
   (e) extracting said aqueous mixture relatively rich in monovalent phenols with the extraction solvent to extract said monovalent phenols and form a further solvent consisting of monovalent phenols and said extraction solvent;
   (f) extracting the scrubbing aqueous mixture separately from the aqueous mixture relatively rich in monovalent phenols with the further solvent produced in step (e) to extract the polyvalent phenols in said further solvent and leaving monovalent phenols in said scrubbing aqueous mixture; and
   (g) extracting monovalent phenols with fresh extraction solvent from said scrubbing aqueous mixture after step (f) and combining the resulting mixture of extraction solvent and monovalent phenols with the further solvent used in step (f).

2. The process defined in claim 1 wherein the extraction solvent is selected from the group which consists of: diisopropyl ether, n-butylacetate, isobutylacetate, methyl-isobutyl ketone, benzene and a water-insoluble, straight or branched chain $C_5$ to $C_{11}$ alcohol.

3. The process defined in claim 1 wherein the extraction solvent is n-butylacetate.

4. The process defined in claim 1 wherein in step (b) NaOH is added to the scrubbing water.

5. The process defined in claim 1 wherein in step (c) a gas condensate having a high $NH_3$ content is obtained from the cooler part of the gas cooler used in step (c) for use as scrubbing water.

6. The process defined in claim 1 wherein in steps (f) and (g) the polyvalent phenols are extracted with further solvent in four to ten stages and the monovalent phenols are subsequently extracted in four to ten stages with the extraction solvent.

7. The process defined in claim 1 wherein the scrubbing water used in step (b) corresponds to 5 to 30% of the condensate formed in step (d).

* * * * *